(12) United States Patent
Hatlestad et al.

(10) Patent No.: US 8,831,716 B2
(45) Date of Patent: Sep. 9, 2014

(54) HISTOGRAM-BASED THORACIC IMPEDANCE MONITORING

(75) Inventors: John D. Hatlestad, Maplewood, MN (US); Cal Roeske, Eagan, MN (US); Loell Boyce Moon, Ham Lake, MN (US); Jeffrey P. Cook, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1197 days.

(21) Appl. No.: 11/853,590

(22) Filed: Sep. 11, 2007

(65) Prior Publication Data

US 2009/0069708 A1   Mar. 12, 2009

(51) Int. Cl.
| | |
|---|---|
| A61B 5/05 | (2006.01) |
| A61B 5/00 | (2006.01) |
| A61B 5/053 | (2006.01) |
| A61N 1/365 | (2006.01) |
| A61B 5/08 | (2006.01) |

(52) U.S. Cl.
CPC ........... *A61B 5/0535* (2013.01); *A61N 1/36521* (2013.01); *A61B 5/6846* (2013.01); *A61B 5/0537* (2013.01); *A61B 5/08* (2013.01); *A61B 5/416* (2013.01)
USPC ....................................................... 600/547

(58) Field of Classification Search
CPC ...... A61B 5/08; A61B 5/0535; A61B 5/0537; A61B 5/416; A61B 5/6846; A61N 1/36521
USPC .......... 600/547, 529, 538, 484; 607/17, 28, 4, 607/5, 7, 9, 11, 27
See application file for complete search history.

(56) References Cited

U.S. PATENT DOCUMENTS

| | | | |
|---|---|---|---|
| 5,282,840 | A | 2/1994 | Hudrlik et al. |
| 5,507,785 | A | 4/1996 | Deno |
| 5,522,860 | A | 6/1996 | Molin et al. |
| 5,562,712 | A | 10/1996 | Steinhaus et al. |
| 5,788,643 | A | 8/1998 | Feldman |
| 5,876,353 | A | 3/1999 | Riff |
| 5,957,861 | A | 9/1999 | Combs et al. |
| 6,104,949 | A | 8/2000 | Pitts Crick et al. |
| 6,449,509 | B1 | 9/2002 | Park |
| 6,473,640 | B1 | 10/2002 | Erlebacher |

(Continued)

FOREIGN PATENT DOCUMENTS

| | | |
|---|---|---|
| EP | 1604705 | 12/2005 |
| EP | 1604705 A1 | 12/2005 |
| WO | WO-2009/035596 A1 | 3/2009 |

OTHER PUBLICATIONS

"International Application Serial No. PCT/US2008/010559, International Search Report mailed Jan. 14, 2009"; 6 pgs.

(Continued)

*Primary Examiner* — Brian Szmal
(74) *Attorney, Agent, or Firm* — Schwegman Lundberg & Woessner, P.A.

(57) ABSTRACT

Systems and methods for monitoring pulmonary edema or other thoracic fluid status in a subject use thoracic impedance histogram information. An internal or external processor circuit receives the thoracic impedance histogram information and uses it to compute and provide a lung fluid status indication. The thoracic impedance histogram information can include a count, mean or median of a histogram bin or subrange of bins within the histogram range.

26 Claims, 10 Drawing Sheets

(56) References Cited

U.S. PATENT DOCUMENTS

| | | |
|---|---|---|
| 6,512,949 B1 | 1/2003 | Combs et al. |
| 6,595,927 B2 | 7/2003 | Pitts-Crick et al. |
| 6,643,543 B2 | 11/2003 | Takehara et al. |
| 6,714,813 B2 | 3/2004 | Ishigooka et al. |
| 6,752,765 B1 | 6/2004 | Jensen et al. |
| 6,829,503 B2 | 12/2004 | Alt |
| 7,149,573 B2 | 12/2006 | Wang |
| 7,413,549 B1 * | 8/2008 | Koh .......................... 600/529 |
| 7,778,708 B1 | 8/2010 | Koh et al. |
| 2004/0102712 A1 | 5/2004 | Belalcazar et al. |
| 2004/0172080 A1 | 9/2004 | Stadler et al. |
| 2005/0065555 A1 | 3/2005 | Er |
| 2005/0080460 A1 | 4/2005 | Wang et al. |
| 2005/0119586 A1 | 6/2005 | Coyle et al. |
| 2005/0137480 A1 | 6/2005 | Alt et al. |
| 2006/0184060 A1 | 8/2006 | Belalcazar et al. |
| 2006/0241513 A1 | 10/2006 | Hatlestad et al. |
| 2007/0179389 A1 | 8/2007 | Wariar |
| 2007/0213599 A1 | 9/2007 | Siejko et al. |
| 2007/0282185 A1 | 12/2007 | Belalcazar |

OTHER PUBLICATIONS

"International Application Serial No. PCT/US2008/010559, Written Opinion mailed Jan. 14, 2009", 9 pgs.

"European Application Serial No. 08830150.2, Office Action mailed Sep. 22, 2010", 6 Pgs.

"Australian Application Serial No. 2008299959, Response and Second Statement of Proposed Amendments filed Jul. 8, 2011 to Examiner Report dated Jan. 27, 2011", 18 pgs.

"Australian Application Serial No.2008299959, Examiner's First Report mailed Jan. 27, 2011", 3 pgs.

"European Application Serial No. 08830150.2, Response filed Feb. 2, 2011 to Office Action mailed Sep. 22, 2010", 19 pgs.

Siejko, Kryzysztof Z., et al., "Physiological Event Detection Systems and Methods", U.S. Appl. No. 11/276,735, filed Mar. 13, 2006, 56 Pages.

\* cited by examiner

HISTOGRAM-BASED THORACIC IMPEDANCE MONITORING

TECHNICAL FIELD

This patent document pertains generally to medical systems and methods. More particularly, but not by way of limitation, this patent document pertains to fluid monitoring systems and methods configured for using histogram-based information about one or more thoracic impedance-indicative signal values to compute and provide a lung fluid status indication.

BACKGROUND

Excess thoracic fluid retention can take various forms and can have different causes. As an example, eating salty foods can result in retaining excess fluid in the thorax and elsewhere. Another source of thoracic fluid accumulation is pulmonary edema, which involves a build-up of extravascular fluid in or around a subject's lungs.

One cause of pulmonary edema is congestive heart failure ("CHF"), sometimes referred to simply as "heart failure." Heart failure is a major health problem—it is estimated that 5 million people suffer heart failure in the United States alone and it is believed to be growing at an approximate rate of 550,000 new cases each year due to, among other things, overall demographic aging. CHF can be conceptualized as an enlarged weakened heart muscle. The impaired heart muscle results in poor cardiac output of blood. Consequently, pulmonary vascular pressures may be elevated to the point that fluid leaks from the pulmonary capillaries into the lungs, affecting normal oxygen exchange. For this reason, pulmonary edema can be an indicator of CHF.

Pulmonary edema can present a medical emergency that requires immediate care. The outlook for pulmonary edema patients can be good if detected early and treated promptly. If left undetected, and consequently untreated, pulmonary edema can lead to extensive hospitalization and even death.

OVERVIEW

The present inventors have recognized, among other things, that one problem presented by worsening heart failure is its timely detection and treatment. The present inventors have further recognized an unmet need for enhanced sensitivity or specificity of ongoing chronic monitoring for actual or impending excess fluid accumulation in the thoracic region of a subject, such as the subject's lungs, before the need for hospitalization arises.

The present systems and methods can monitor lung fluid status, such as the presence or absence of pulmonary edema, in a subject. This can involve using information about at least one thoracic impedance-indicating signal characteristic. The impedance characteristic information can be stored histogram bins. Each histogram bin can represent a numerical subrange of an array of expected thoracic impedance-indicating signal characteristic values. Each histogram bin can be configured to quantifiably store the occurrence of numerically inclusive thoracic impedance-indicating characteristic signals measured by an electrical impedance measurement circuit. In various examples, an internal or external processor circuit includes an input to receive information about one or more histogram bins or the characteristic signal(s) stored therein. The processor circuit can be configured to use such information to compute and provide a lung fluid status indication. In some examples, the information about the histogram bin(s) used to compute the lung fluid status indication includes a count, mean, or median of the thoracic impedance-indicating signal characteristic value(s) stored therein.

In Example 1, a system comprises an implantable medical device including, an electrical impedance measurement circuit configured to measure at least one thoracic impedance-indicating signal characteristic using information about electrical energy injected between two or more electrodes and a potential difference created thereby between the same or different two or more electrodes; and a memory circuit including a number of histogram bins, each bin representing a subrange of thoracic impedance-indicating signal characteristic values, the memory circuit configured for storing the at least one thoracic impedance-indicating signal characteristic into a histogram bin having a numerically inclusive subrange; and a processor circuit including an input to receive and use information about the at least one thoracic impedance-indicating signal characteristic stored in the histogram to provide a lung fluid status indication.

In Example 2, the system of Example 1 optionally comprises a trigger circuit to trigger a thoracic impedance-indicating measurement synchronized with a refractory portion of a subject's cardiac cycle, the trigger circuit comprising at least one of a timing circuit or a cardiac sensor circuit.

In Example 3, the system of at least one of Examples 1-2 optionally comprises a posture sensor configured to produce a posture signal indicative of a posture of a subject, the posture sensor configured to trigger a thoracic impedance-indicating measurement when the posture signal is indicative of a substantially upright orientation.

In Example 4, the system of at least one of Examples 1-3 is optionally configured such that the memory circuit includes a counter circuit configured to increment a count of a histogram bin.

In Example 5, the system of Example 4 is optionally configured such that the processor circuit is configured to use information about the count of the histogram bin to compute and provide the lung fluid status indication.

In Example 6, the system of at least one of Examples 1-5 optionally comprises a histogram-selective circuit configured to select one or more histogram bins representative of a reduced subrange of the histogram.

In Example 7, the system of Example 6 is optionally configured such that the processor circuit is configured to use information about the reduced subrange to compute and provide the lung fluid status indication, the reduced subrange representing an upper-percentile of the histogram or an intra-percentile range of the histogram.

In Example 8, the system of Example 7 is optionally configured such that the information about the reduced subrange includes information about a central tendency of information represented by the reduced subrange.

In Example 9, the system of at least one of Examples 1-8 optionally comprises a comparator circuit configured to compute a deviation between one or more histogram bins previously received from the memory circuit and one or more corresponding baseline histogram bins having substantially the same numerical subrange; the processor circuit optionally configured to use information about the deviation to compute and provide the lung fluid status indication.

In Example 10, the system of Example 9 is optionally configured such that the deviation is indicative of a difference in the number of counts from the corresponding baseline histogram bin.

In Example 11, the system of Example 9 is optionally configured such that the deviation is between an average of thoracic impedance signal characteristic data of the one or more histogram bins previously received and thoracic impedance signal characteristic data of the one or more baseline histogram bins.

In Example 12, the system of at least one of Examples 1-11 optionally comprises an external user-interface device communicatively coupled to the implantable medical device and including a user-detectable indication, the user-detectable indication configured to provide a display of at least one of received information about thoracic impedance signal characteristic data of one or more histogram bins, a deviation trend between such received information and corresponding information of one or more baseline histogram bins, or the computed lung fluid status indication.

In Example 13, a method comprises measuring a thoracic impedance-indicating signal characteristic including a fluid status component; storing the thoracic impedance-indicating signal characteristic in a histogram that includes a plurality of histogram bins representing corresponding subranges of thoracic impedance-indicating signal characteristic values; and computing and providing a lung fluid status indication using histogram information about the thoracic impedance-indicating signal characteristic.

In Example 14, the method of Example 13 optionally comprises attenuating a cardiac stroke component of the thoracic impedance-indicating signal.

In Example 15, the method of Example 14 is optionally configured such that attenuating the cardiac stroke component includes synchronizing the thoracic impedance-indicating signal measurement to a specified portion of a subject's cardiac cycle.

In Example 16, the method of at least one of Examples 13-15 optionally comprises selecting one or more histogram bins representative of a subrange of the histogram; and using information about the one or more bins representative of the subrange to provide the lung fluid status indication.

In Example 17, the method of at least one of Examples 13-16 optionally comprises overwriting a first histogram comprising first histogram bins with a second histogram comprising second histogram bins, the second histogram comprising data acquired later in time than for the first histogram array.

In Example 18, the method of at least one of Examples 13-17 optionally comprises alerting a subject to the presence of thoracic fluid accumulation using the lung fluid status indication.

In Example 19, the method of at least one of Examples 13-18 optionally comprises initiating or adjusting a regimen in response to the lung fluid status indication.

In Example 20, the method of at least one of Examples 13-19 optionally comprises triggering the thoracic impedance-indicating signal characteristic measurement when a posture signal indicative of a substantially upright orientation is measured.

In Example 21, the method of at least one of Examples 13-20 is optionally configured such that storing the thoracic impedance-indicating signal characteristic includes incrementing a count associated with a histogram bin; and computing the lung fluid status indication includes using count information from the histogram.

In Example 22, the method of Example 21 optionally comprises aggregating count information from each of the histogram bins; and using the aggregated count information to compute the lung fluid status indication.

In Example 23, the method of at least one of Examples 13-22 is optionally configured such that storing the thoracic impedance-indicating signal characteristic includes storing the thoracic impedance-indicating signal characteristic into a bin of an intraday histogram.

In Example 24, the method of Example 23 optionally comprises aggregating thoracic impedance-indicating signal characteristic information from a plurality of intraday histograms; and using the aggregated thoracic impedance signal characteristic information to compute the lung fluid status indication.

In Example 25, the method of at least one of Examples 13-24 is optionally configured such that computing the lung fluid status indication includes computing a deviation between at least one histogram bin of a short-term histogram and at least one corresponding histogram bin of a baseline histogram.

In Example 26, the method of Example 25 optionally comprises updating the short-term histogram using a thoracic impedance-indicating signal characteristic measured over a first time period; and updating the baseline histogram using a thoracic impedance-indicating signal characteristic measured over a second time period that is longer than the first time period.

In Example 27, the method of at least one of Examples 13-26 is optionally configured such that computing the lung fluid status indication includes recognizing whether a thoracic fluid accumulation event is present.

In Example 28, the method of at least one of Examples 13-27 is optionally configured such that computing the lung fluid status indication includes recognizing whether pulmonary edema is present.

In Example 29, a system comprises means for measuring a thoracic impedance-indicating signal characteristic including a fluid status component; means for storing the thoracic impedance-indicating signal characteristic in a histogram that includes a plurality of histogram bins representing corresponding subranges of thoracic impedance-indicating signal characteristic values; and means for computing and providing a lung fluid status indication using histogram information about the thoracic impedance-indicating signal characteristic.

The present systems and methods can enhance thoracic fluid monitoring by reducing data storage or signal processing needed. This can reduce implanted device size or increase its longevity. The foregoing can be made possible by, among other things, storing information about at least one thoracic impedance-indicating signal characteristic in one of a number of histogram bins. Each histogram bin can numerically represent a different subrange of thoracic impedance-indicating signal characteristic values from an expected range. Thoracic fluid monitoring complexity can be reduced by using information about a count of thoracic impedance signal characteristic values stored in one or more of the histogram bins to compute a lung fluid status indication. Thoracic fluid monitoring can also be made more accurate, such as by using information about a selected portion of a histogram array. For example, information about an upper-quartile portion or intra-quartile portion of the histogram array can be used to compute the lung fluid status indication.

These and other examples, advantages, and features of the present fluid monitoring systems and methods will be set forth in part in following Detailed Description. This Overview is intended to provide an overview of subject matter of the present patent application. It is not intended to provide an exclusive or exhaustive explanation of the invention. The Detailed Description is included to provide further information about the present patent application.

BRIEF DESCRIPTION OF THE DRAWINGS

In the drawings, like numerals may be used to describe similar components throughout the several views. Like numerals having different letter suffixes may be used to represent different instances of similar components. The drawings illustrate generally, by way of example, but not by way of limitation, various embodiments discussed in the present document.

DETAILED DESCRIPTION

Excess fluid accumulation in a region of a subject is typically referred to simply as "edema." Edema can be conceptualized as a failure or decompensation of one or more homeostatic processes within the subject's body. The body normally prevents the accumulation of fluids therewithin by maintaining adequate pressures and concentrations of salts and proteins, and by actively removing excess fluid. If a disease affects any of these normal bodily mechanisms or if the normal bodily mechanisms are unable to keep up with the fluid accumulation, the result can be edema, such as pulmonary edema.

Figure 1:
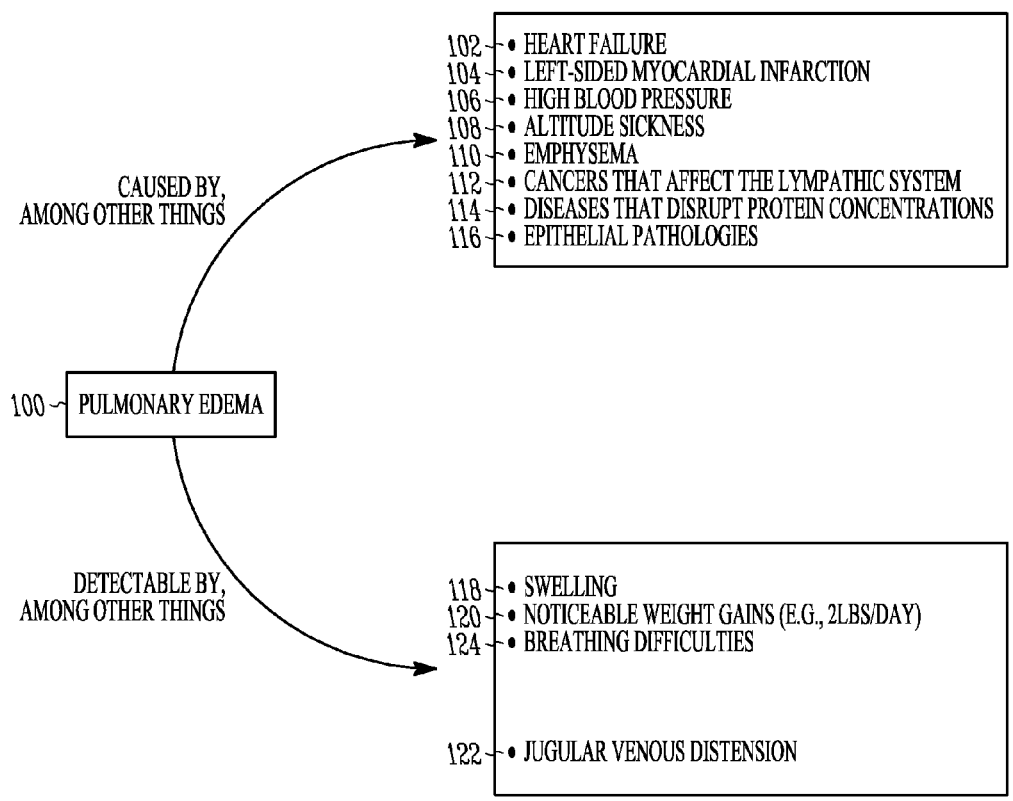
FIG. 1 is a block diagram illustrating examples of various causes and indications of pulmonary edema in a subject.

There are several conditions or diseases that can cause or affect pulmonary edema. As shown in FIG. 1, this includes, among others, heart failure 102, left-sided myocardial infarction 104, high blood pressure 106, altitude sickness 108, emphysema 110, cancers that affect the lymphatic system 112, diseases that disrupt protein concentrations 114, or epithelial pathologies 116, such as those caused by inhalation of toxic chemicals, leading to flooding of the alveoli. While pulmonary edema 100 can be a sign of many conditions or diseases, the prospect that pulmonary edema 100 can be a sign of failing heart circulation 102 is often of first concern to caregivers (e.g., health care professionals) due to the severity of its nature. Unfortunately, the first indication that an attending caregiver typically has of an occurrence of pulmonary edema 100 is very late in the disease process, such as when it becomes physically manifested by swelling 118, noticeable weight gain 120, jugular venous distension 122, or breathing difficulties 124 that are so overwhelming as to be noticed by the subject, who then proceeds to be examined by his or her caregiver. For a heart failure subject, hospitalization at such a physically apparent time will likely be required.

In an effort to timely and accurately detect impending edema, such as pulmonary edema, and avoid its associated hospitalizations, the present ambulatory fluid monitoring systems and methods compute and provide a lung fluid status indication using information about at least one thoracic impedance-indicating signal characteristic stored in one of a number of histogram bins. Each histogram bin represents a numerical subrange of an array of expected thoracic impedance-indicating signal characteristic values, and is configured to quantifiably store the occurrence of numerically inclusive thoracic impedance-indicating signal characteristics measured by an electrical impedance measurement circuit. For each thoracic impedance-indication signal characteristic value stored in a given histogram bin, a count of values for that bin is incremented. Thus, over a given time period, many measurements can be efficiently stored. This histogram-based information, upon storing, can thereafter be used to estimate the probability distribution or summary statistics of thoracic impedance-indicating values for the given time period. This can be used to compute and provide a lung fluid status indication having potentially enhanced sensitivity (e.g., effectively detect a condition that a user desired to detect or treat) or specificity (e.g., avoid erroneous or "false" detections of the condition that a user desires to detect or treat).

EXAMPLES

Figure 2:
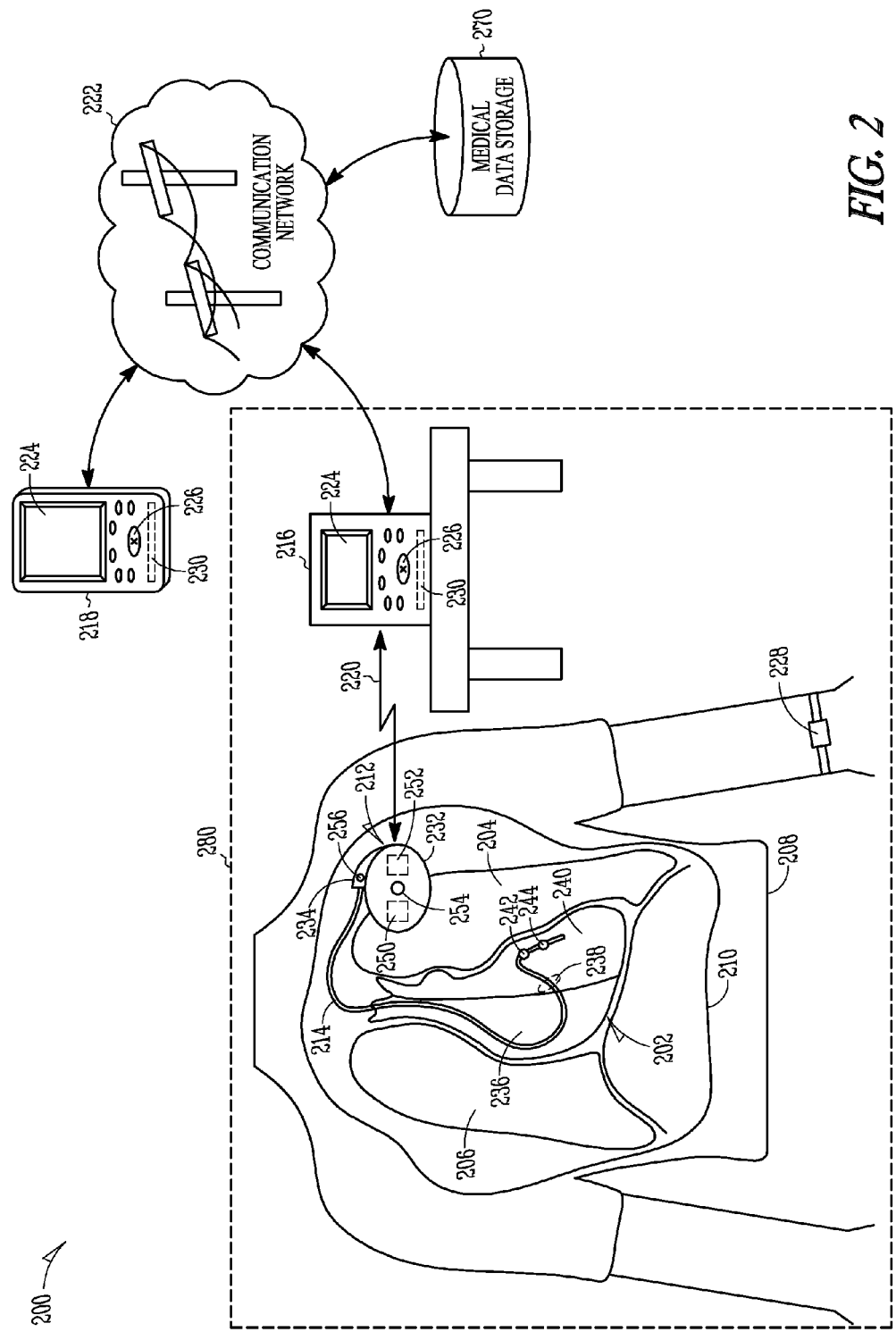
FIG. 2 is a schematic view of an example of a system configured for monitoring excess fluid accumulation in the thoracic region of a subject by computing and providing a lung fluid status indication, the indication found using information organized and stored in one or more histogram bins.

FIG. 2 shows a heart 202 and lungs 204 (left), 206 (right) of a subject 208 (via a cut-away portion 210), and an example of an ambulatory system 200 configured for monitoring excess fluid accumulation in a thoracic region, such as the lungs. The monitoring can use information about at least one thoracic impedance-indicating signal characteristic implantably stored in one of a plurality of histogram bins. In various examples, such monitoring can occur in the comfort of one's own home 280. Each histogram bin represents a numerical subrange of a range of thoracic impedance-indicating signal characteristic values. Each histogram bin can be configured to quantifiably store the occurrence of numerically inclusive thoracic impedance-indicating signal characteristics, such as can be measured by an electrical impedance measurement circuit.

In FIG. 2, the system 200 includes a pectorally-implanted medical device (IMD) 212, which is coupled via one or more electrode-bearing leads 214 to the heart 202 of the subject 208. In this example, the system 200 can also include one or more programmers, medical data storage systems 270, or other external user-interface devices 216 (nearby), or 218 (distant) providing communications with the IMD 212, such as by using telemetry 220 or another communication network 222. As shown, the one or more external user-interface devices 216, 218 can include, among other things, a user-detectable indication 224, a user input device 226, and a processor circuit 230. The user-detectable indication 224, such as an LCD or LED or other display, can textually or graphically relay information collected by the IMD 212 or information about a lung fluid status indication computed by the processor circuit 230 using the IMD collected information. The user input device 226 is configured for receiving programming information from a user and communicating the programming information to the IMD 212. A wearable device 228 can be used to extend the communications range between the IMD 212 and the nearby external user-interface device 216 or the communication network 222 without substantially increasing battery usage of the IMD 212.

As shown, the IMD 212 can include a housing 232 that houses the electrical impedance measurement circuit 250 configured for measuring the at least one thoracic impedance-indicating signal characteristic and a memory circuit 252 configured for implantably storing the at least one thoracic impedance-indicating signal characteristic in one of a number of histogram bins having a numerically inclusive subrange. The IMD 212 can include a left ventricular port in a header 234 thereof for receiving a proximal end of an electrode-bearing left ventricular lead 214. A distal end of the left ventricular lead 214 can be introduced into the venous system, down the superior vena cava, into the right atrium 236, into a coronary sinus through an orifice 238, and then further into a coronary vein, which runs epicardially over the left ventricle 240.

In the example shown, the left ventricular lead 214 includes two electrodes 242, 244 that are electrically connected to respective conductors that run through the lead 214. The conductors connect to conducting wires within the IMD 212 when the left ventricular lead 214 is received by the left ventricular lead port, thereby establishing electrical connections between the electrical impedance measurement circuit 250 and the electrodes 242, 244. In this example, the electrode 242 can be referred to as a left ventricular proximal electrode, while electrode 244 can be referred to as a left ventricular distal electrode, due to their relative positioning on the left ventricular lead 214. While the left ventricular lead 214 shown in FIG. 2 is bipolar in nature, the lead 214 can optionally include additional or fewer electrodes and can further follow a different path through the heart 202 from that shown and described.

A housing electrode 254 on an exterior surface of the IMD housing 232 can be electrically connected to the electrical impedance measurement circuit 250 to complete a tripolar electrode configuration in which electrical energy (e.g., current) is injected between a lead electrode, such as the left ventricular distal electrode 244, and the housing electrode 254, and a potential difference (i.e., voltage) created by the injected energy can be measured between the other lead electrode—in this example, the left ventricular proximal electrode 242—and the housing electrode 254. The IMD 212 can optionally include a second housing or header electrode 256 to facilitate a tetrapolar electrode configuration in which electrical energy is injected, for example, between a the left ventricular distal electrode 244 and the housing electrode 254, and a responsive potential difference created by the energy is measured between the left ventricular proximal electrode 242 and the header electrode 256. Using information about the injected electrical energy and the resulting potential difference, an impedance calculator (e.g., within the electrical impedance measurement circuit 250) can calculate a thoracic impedance-indicating signal characteristic such as by taking the ratio of measured voltage to injected current. An impedance-indicating signal characteristic, such as amplitude of the impedance signal, for example, can then be communicated to memory 252 for storing in the appropriate one of a number of histogram bins, such as by incrementing the count of the histogram bin representing an impedance range into which the measured impedance amplitude falls.

Figure 3:
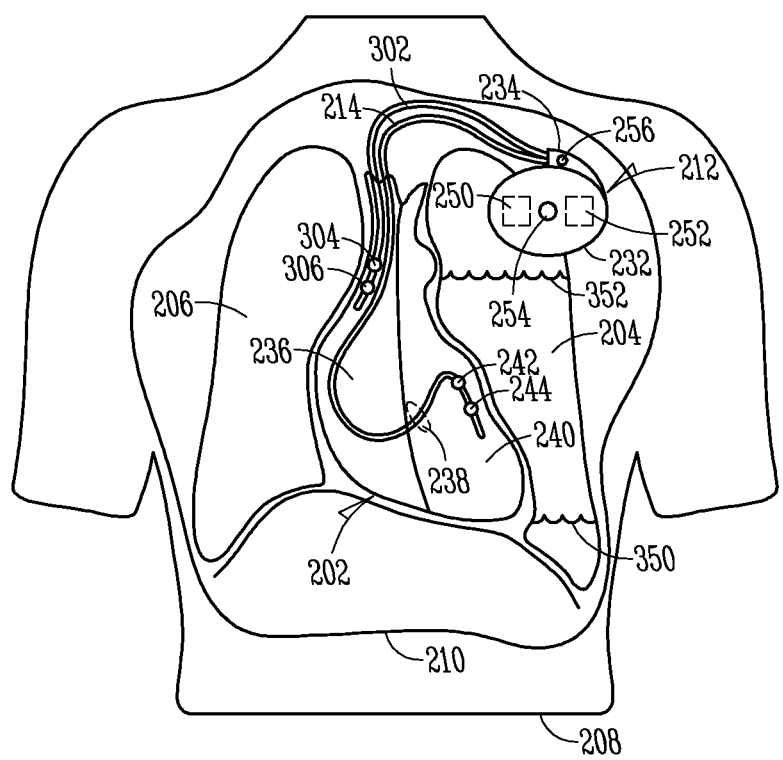
FIG. 3 is a schematic view illustrating an example implant site of portions of a system configured for monitoring excess fluid accumulation in the thoracic region of a subject by computing and providing a lung fluid status indication, the indication found using information organized and stored in one or more histogram bins.

FIG. 3 illustrates that the IMD 212 can include not only a left ventricular port in the header 234 thereof for receiving the proximal end of the left ventricular lead 214, but can also include a right atrial port for receiving a proximal end of an electrode-bearing right atrial lead 302. A distal end of the right atrial lead 302 is shown in this example as being introduced into the venous system, down the superior vena cava, and into the right atrium 236. In the example shown, the right atrial lead 302 includes two electrodes 304, 306 that are electrically connected to conductors that run through the lead 302. The conductors connect to conducting wire within the IMD 212 when the right atrial lead 302 is received by the right atrial lead portion, thereby establishing electrical connections between the electrical impedance measurement circuit and the electrodes 304, 306. In this example, the electrode 304 can be referred to as a right atrial proximal electrode, while electrode 306 can be referred to as a right atrial distal electrode, due to their relative positioning on the right atrial lead 302. While the right atrial lead 302 shown in FIG. 3 is bipolar in nature, the lead 302 can optionally include additional or fewer electrodes and can follow a different path through the heart 202 from that shown.

Including the right atrial lead 302 in FIG. 3 provides a tetrapolar electrode configuration for measuring thoracic impedance-indicating signal characteristics. In such an example, electrical energy can be injected between the housing electrode 254 and the left ventricular distal electrode 244. A potential difference created by the energy can be measured between left ventricular proximal electrode 242 and one of the right atrial proximal electrode 304 or the right atrial distal electrode 306. In this example, should the left ventricular lead 214 not be available, thoracic impedance-indicating signal characteristics can still be measured, such as by injecting electrical energy between the housing electrode 254 and the right atrial distal electrode 306. A potential difference created by the energy can be measured between the housing 254 or header 256 electrode and the right atrial proximal electrode 304.

The human body includes a number of thoracic organs, tissues, and fluids. Measurement of thoracic impedance can include contributions from each. For example, resistivities of the heart muscle, lungs, pectoral muscle, pectoral fat, liver, kidneys, spleen, stomach, skeletal muscle, bone, cartilage, blood and other tissues and fluids each can contribute to a measurement of thoracic impedance. As such, changes in measured thoracic impedance can be caused by changes in the resistivities of these and other organs or tissues.

Thus, when measuring impedance, such as thoracic impedance, to detect or assess one or more pathologies or conditions, such as pulmonary edema, it can be desirable to measure the impedance-indicating signals using one or more electrode configurations that are more sensitive to a particular region(s) of interest. In the examples of FIGS. 2-3, placement of the left ventricular lead 214 and the right atrial lead 302 near the left ventricle 240 and the right atrium 236 of the heart 202, respectively, provide an example of a suitable location for measuring thoracic impedance, and more specifically heart and lung impedance, due to the proximity of the heart and lungs 204, 206 thereto. Although not shown, a right ventricular lead having right ventricular electrodes can also be used in one or more thoracic impedance measurement configurations.

In various examples, the electrical impedance measurement circuit 250 within the IMD 212, in conjunction with the lead 214, 302, header 256, or housing 254 electrodes, measure thoracic impedance-indicating signal characteristics by injecting a relatively small amplitude electrical energy (e.g., a current) between at least two implanted electrodes and concurrently measuring an responsive induced potential difference (i.e., a voltage) between the same or different at least two implanted electrodes, such as discussed above. Because the magnitude of the injected electrical energy is typically specified, the measurement of the responsive potential difference allows for a thoracic impedance-indicating signal characteristic measurement to be determined, such as from Ohm's law (e.g., by taking a ratio of measured voltage to injected current).

In various examples, the thoracic impedance-indicating signal characteristic measured includes—listed in order from generally higher frequencies to generally lower frequencies—information about the subject's heart contractions (stroke component), the subject's breathing (respiration component), and the subject's edema (fluid status component). As fluid accumulates in the lungs due to pulmonary edema, such as from a low fluid level to a higher fluid level, the impedance-indicating signal decreases in value permitting pulmonary edema to be detected. Without being bound by theory, it is believed that the respiration component may also be affected by thoracic fluid accumulation.

The IMD 212 can include one or both of a timing or cardiac sensor circuit (see FIG. 5A) to synchronize impedance sampling to occur at a particular portion of the subject's cardiac cycle, such as within a refractory portion of the subject's cardiac cycle. During such refractory periods, sense amplifiers for detecting the intrinsic electrical heart signals are "blanked" or otherwise configured to be less likely to detect intrinsic electrical depolarizations that are indicative of intrinsic heart contractions. This avoids the possibility of the delivered test current somehow being erroneously detected by such sense amplifiers as indicating an intrinsic electrical depolarization corresponding to an intrinsic heart contraction. Such an erroneous detection, in turn, could trigger delivery of inappropriate responsive therapy. Synchronizing thoracic impedance sampling to a refractory portion of a cardiac cycle is consistent with established techniques for thoracic impedance sampling, such as thoracic impedance determination of a minute ventilation signal for controlling pacing rate of a rate-responsive pacer. Because no analogous difficulties exist with respect to the respiration component of the thoracic impedance signal, the measured thoracic impedance signal need not be synchronized to a particular portion of the respiration cycle of the measured thoracic impedance signal. Therefore, the measured impedance signal generally can include at least a respiration component.

Figure 4:
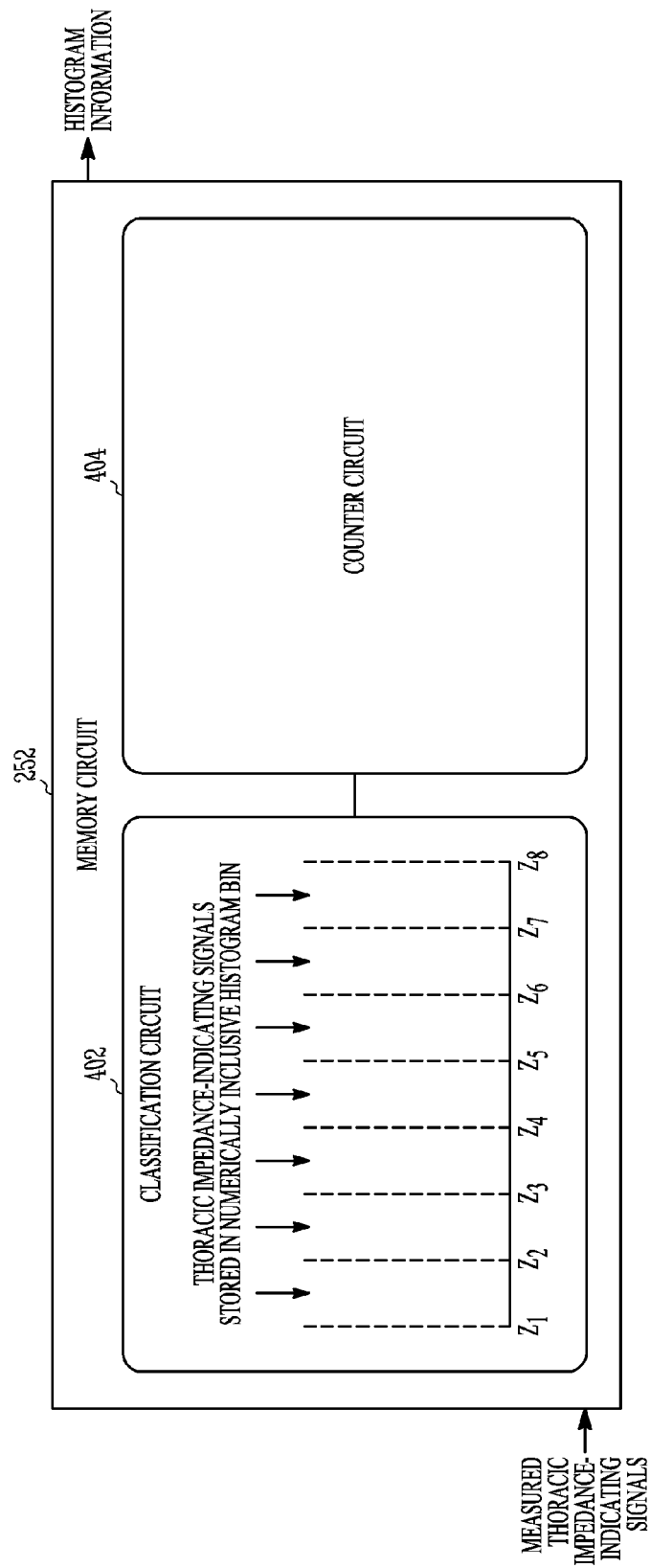
FIG. 4 is a block diagram illustrating an example of an implantable memory circuit used by a fluid monitoring system to organize and store at least one thoracic impedance-indicating signal in one of a number of histogram bins.

FIG. 4 is a block diagram illustrating one conceptual example of an implantable memory circuit 252 that can be used by the present fluid monitoring system 200. A classification circuit 402 of the memory circuit 252 is configured to organize and store digitized thoracic impedance-indicating signal characteristic measurements in one of a number of bins collectively comprising a histogram. The histogram can be divided into a programmable number of bins (e.g., 255 bins). Each bin can represent a corresponding subrange of thoracic impedance-indicating signal characteristic amplitude values. Each bin can also include a corresponding count representing the number of samples detected during a particular time period that fell within the subrange of that bin. In certain examples, this count can be implemented as a memory location storing a count value. In certain examples, such bin count memory locations can be included in a counter circuit 404 that increments the appropriate bin's count of the number of impedance samples falling into that bin's subrange of values. Using the histogram approach, over a given time period many measurements can be efficiently stored in the histogram. The histogram, or portions thereof, can be used to estimate the probability distribution or summary statistics of the impedance values for the given time period.

In an example, the bins collectively form an intraday histogram. The intraday histogram can store part of a day's worth of thoracic impedance-indicating signal characteristic data. A new intraday histogram array can be acquired and populated with impedance signal measurements several times daily, if desired. In some examples, the IMD 212 (FIG. 2) can store about 90 days worth of intraday histograms in a buffer, and after 90 days, can overwrite the oldest histograms with newly acquired histograms. A daily or other short-term histogram can also be computed in certain examples, such as directly or by aggregating that day's intraday histograms, for example. In various examples, an internal or external processor circuit includes an input to receive thoracic impedance histogram information, and is configured to use such information to compute and provide a lung fluid status indication, such as further discussed below.

Figure 5A:
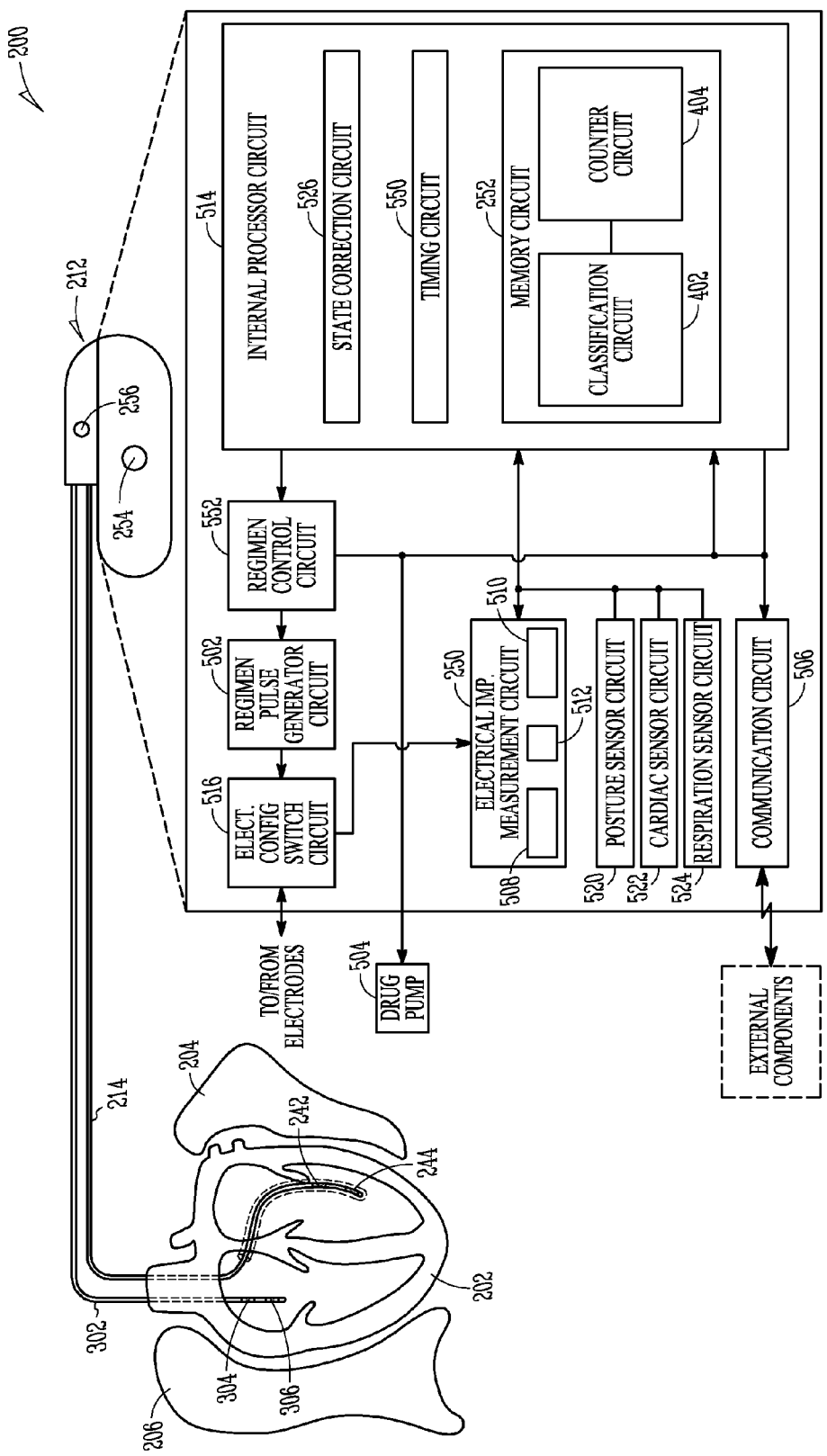
FIGS. 5A-5B are block diagrams illustrating portions of an example system configured for monitoring excess fluid accumulation in the thoracic region of a subject by computing and providing a lung fluid status indication, the indication found using information organized and stored in one or more histogram bins.
Figure 5B:
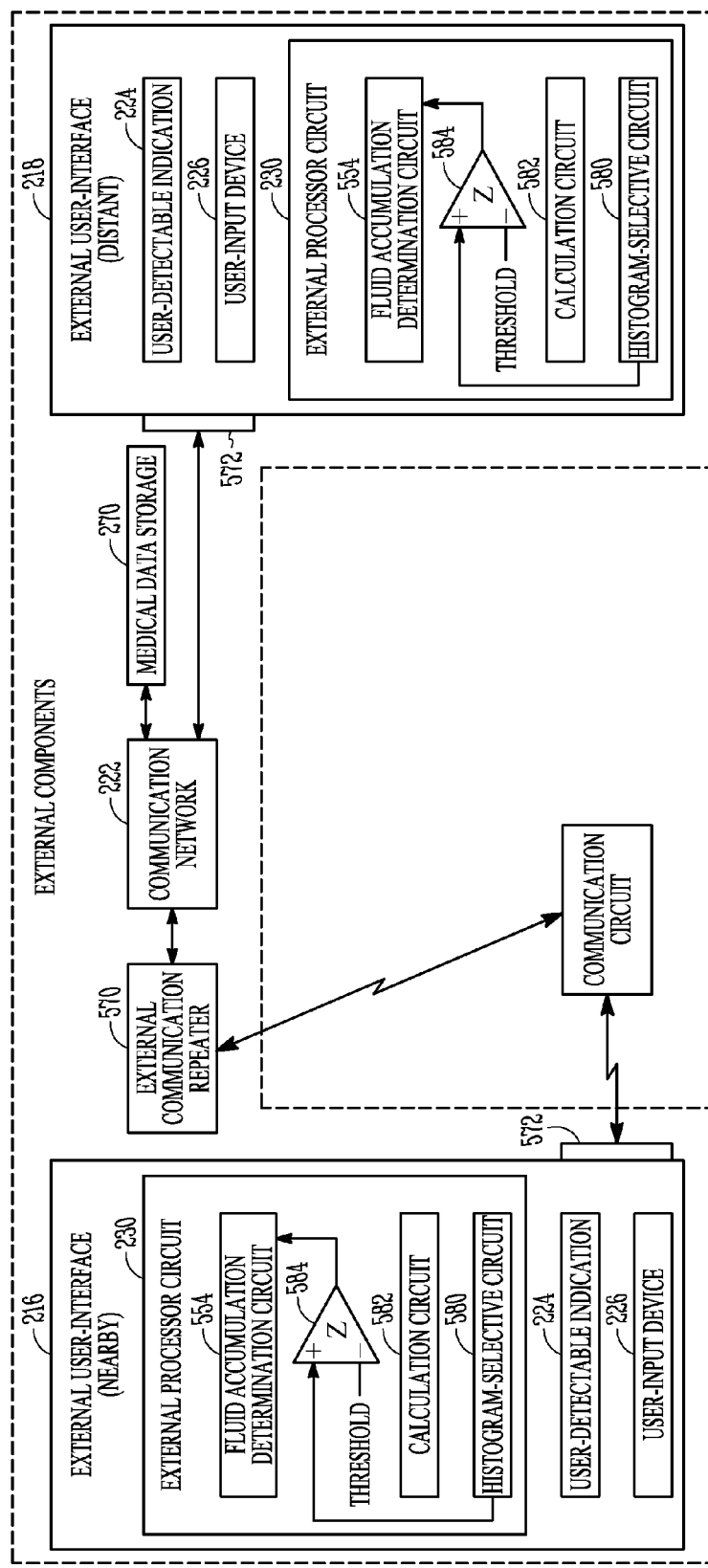

FIGS. 5A-5B are block diagrams illustrating generally, by way of example, but not by way of limitation, portions of an example system 200 configured for using thoracic impedance histogram information for monitoring fluid accumulation status in a subject's thoracic region, such as a subject's left 204 or right 206 lungs. In this example, the system 200 includes a hermetically sealed IMD 212 coupled to a subject's heart 202 such as by one or more electrode-bearing intravascular leads. The example of FIG. 5A illustrates use of a left ventricular lead 214 having electrodes 242, 244 or a right atrial lead 302 having electrodes 304, 306. As shown in FIG. 5B, the system 200 can further include one or more programmers or other external user-interface devices 216 (nearby), 218 (distant). The IMD 212 includes circuitry for, among other things, measuring thoracic impedance-indicating signal characteristics, efficiently storing the impedance-indicating signals, and interfacing with external components.

In the example of FIG. 5A, an electrical impedance measurement circuit 250 can include an injected electrical energy generator circuit 508, a voltage measurement circuit 510, an analog-to-digital (A/D) converter, and a calculation circuit 512 to compute and provide a thoracic impedance-indicating signal characteristic to a memory circuit 252 for efficient storage, as discussed above for FIG. 4. The electrical energy generator circuit 508 can be configured to generate and inject a sub-stimulation current or other electrical energy between at least two electrodes, such as excitation electrodes (e.g., left ventricular distal electrode 244 and can electrode 254). In one example, the injected current is AC in nature and has a frequency of about 4 KHz-100 KHz.

The injection current creates an electric field in a subject's body. Thus, a voltage potential appears between, for example, the left ventricular proximal electrode 242 and header electrode 256. A voltage measurement circuit 510 is configured to then measure this voltage between electrodes 242 and 256, for example. The voltage measurement circuit 510 can include a demodulator. In various examples, the particular electrodes used to inject the energy and to measure the resulting potential difference can be selected by an electrode configuration switch circuit 516.

The calculation circuit 512 receives, measures, or includes information on the magnitudes of both the injected current and the resulting measured voltage. An analog-to-digital (A/D) converter, within or outside of the calculation circuit 512, can be used to translate the information. Other signal processing or frequency-selective filtering can (but need not) be performed. Once digitized, these values can be applied as inputs to the calculation circuit 512 for calculating a thoracic impedance-indicating signal characteristic, such as by dividing the measured voltage by the injected current. As body tissue fluid levels increase, the tissue impedance decreases. Thus, the impedance can be used to assess pulmonary edema, and a degree of pulmonary edema can be determined for the subject.

Information from one or more sensor circuits, such as a posture sensor circuit 520, a cardiac sensor circuit 522, or a respiration sensor circuit 524, can be input to an internal processor circuit 514 and used to adjust the relationship (via a state correction circuit 526) between the measured thoracic impedance-indicating signal characteristics and the degree of edema or ensure certain impedance sampling parameters are met. For instance, the posture sensor circuit 520 may provide subject orientation information to the state correction circuit 526. This allows posture compensation to be included in the assessment of edema. Because organs and excess fluid in the thorax and lungs can shift with posture changes due to gravity, measured impedance may vary as a subject 208 (FIG. 2) assumes different positions. For example, when a subject 208 lies on his/her right side, fluid and tissues in the left lung 204 may gravitate towards the mediastinum near the left ventricular lead electrodes 242, 244 resulting in lower measured impedance. Thus, based on posture sensor information, the relationship between the impedance-indicating signal measurement and the degree of edema may be adjusted to compensate. Similarly, that relationship may be inversely adjusted for a subject lying on his/her left side. One or more of several types of posture sensors could be used, including one or any combination of a mercury switch, a tilt switch, a single axis accelerometer, a multi-axis accelerometer, or piezoresistive or other devices.

A respiration sensor circuit 524, such as a minute ventilation (MV) sensor, motion sensor, strain gauge on the diaphragm, or other activity sensor, can also provide information to the state correction circuit 526. The respiration sensor circuit 524 can provide breathing cycle information to the state correction circuit 526. This information can be used for verifying that an impedance sampling period is greater a corresponding respiration cycle, such as to ensure that one or more respiratory components are retained and included in the thoracic-impedance indicating signal, if desired.

The IMD 212 can further include a timing 550 or other circuit, such as the cardiac sensor circuit 522 that can detect cardiac rate or amplitude, such as to synchronize impedance sampling to a specified portion (e.g., a refractory portion) of the subject's cardiac cycle. This helps reduce the chance of the delivered impedance test current being erroneously detected as a heart depolarization by sense amplifiers for detecting intrinsic electrical heart signals. Any of the sensors 520, 522, or 524 can optionally be excluded from the IMD 212.

A communication circuit 506 within the IMD 212 can be configured for wirelessly communicating with a communication circuit of the nearby external user-interface device 216.

In certain examples, the communication circuit 506 is configured for wirelessly communicating with a communication circuit of a distant external user-interface device 218, such as by using a nearby external communication repeater 570. In one such example, the external communication repeater 570 is coupled to the distant external user-interface device 218 such as via an Internet or telephone communication network 222. The Internet or telephone communication network 222, in certain examples, allows the external communication repeater 570 to communicate with electronic medical data storage system 270.

The external user-interface devices 216, 218 can include, among other things, an input 572 to receive thoracic impedance histogram information from the memory circuit 252 and an external processor circuit 230 to use such received information to compute and provide a lung fluid status indication. The external user-interface devices 216, 218 can further include a user-detectable indication 224, such as for textually or graphically relaying information collected via input 572 or information about the lung fluid status indication computed by the processor circuit 230. In addition, the external user-interface devices 216, 218 can include a user input device 226 for receiving programming information from a user and communicating the programming information to the IMD 212.

To compute and provide the lung fluid status indication, the external processor circuit 230 can include a histogram-selective circuit 580, a calculation circuit 582, a comparator circuit 584, and a fluid accumulation determination circuit 554. The histogram-selective circuit 580 can be configured to select one or more histogram bins representative of certain histogram portion, such as an upper-quartile histogram portion, for use in computing the lung fluid status indication. The calculation circuit 582 can be configured to receive the selected one or more histogram bins to extract a signal count or compute a mean or median or other measure of central tendency of thoracic impedance-indication signal characteristic counts stored in such bins such as by using statistical analysis.

The count, mean, median or the like can then be output to the comparator circuit 584, such as for comparison with a stored specified baseline threshold, algorithm, pattern, or histogram, each of which can be based on a subject in a non-edemic state. An initial stored baseline can be preprogrammed into the comparator 584, and thereafter adjusted up and down using recently measured and stored thoracic impedance-indicating signal characteristic data. It can be determined whether the output data exhibits a characteristic of present or impending lung fluid accumulation, such as an indication that a deviation between the output data and the baseline is beyond some programmed limit, for example. If the deviation extends beyond such limit, the resulting comparison can be forwarded to a fluid accumulation determination circuit 554. The fluid accumulation determination circuit 554 can be configured to use such information to provide a lung fluid status indication, such as an indication of present or impending lung fluid accumulation.

In one example, the comparator circuit 584 is configured to compute a deviation between one or more portions of a daily histogram array and a baseline histogram array using the following equation:

$$\Delta z_n = \frac{1}{C_n} \sum_{i=1}^{I} z_i \left( c_{ni} - \frac{C_n}{B_n} b_{ni} \right),$$ [Equation 1]

where $c_{ni}$ represents the count in the ith histogram bin of the nth day's daily histogram array, $b_{ni}$ represents the count in the ith bin of the baseline histogram array, $C_n$ is the total number of the current day's daily histogram array counts, $B_n$ is the total number of the baseline histogram array counts, I is the total number of histogram array bins, and $z_i$ is the thoracic impedance-indication signal value corresponding to the ith bin. If the above equation yields a value below a specified threshold value, then the fluid accumulation determination circuit 554 declares an indication of fluid accumulation to exist. This indication of fluid accumulation can be the sole basis of issuing an alert to a user, or it can be combined or otherwise used with one or more other indications, referred to as "detection enhancements."

A first such "detection enhancement" integrates a negative difference between $\Delta z_n$ and the specified threshold value, such as over a period of multiple days. If this integrated value exceeds a specified (different) threshold value, then an indication of fluid accumulation is declared.

In a second detection enhancement technique, one or more rules require m out of n of the most recent $\Delta z_n$ samples to meet the specified threshold value before declaring the occurrence of a thoracic fluid accumulation event. In such a case, a single threshold crossing can be referred to as a "tentative event." No alert is provided until m out of the last n days meet the threshold, which is then deemed an actual fluid accumulation event. Multiple such m of n rules may be concurrently employed, e.g. three out of three, three out of four, three out of five, three out of six, four out of seven, etc.

The specified threshold value, to which $\Delta z_n$ is compared, can be obtained using a Constant False Alarm Rate (CFAR) detection technique. At least one example of a suitable CFAR detection technique is described in commonly-owned Siejko et al., U.S. patent application Ser. No. 11/276,735, entitled "PHYSIOLOGICAL EVENT DETECTION SYSTEMS AND METHODS," which is incorporated herein by reference in its entirety. The caregiver specifies a maximum acceptable rate of false alarms (e.g., 1%) that the caregiver is willing to tolerate. If the baseline histogram has been acquired during a time period that is free of any fluid accumulation events, this baseline histogram can be used as a probability density function (PDF). The user-specified maximum acceptable rate of false alarms maps to a tail area under the PDF curve provided by the event-free baseline histogram. A boundary of the tail area corresponds to the specified threshold value, against which $\Delta z_n$ is compared. Thoracic impedance-indicating signal characteristic values detected in the bins corresponding to the defined tail of the distribution represent evidence of fluid accumulation events. Since the baseline histogram can change over time, the specified threshold value can be periodically or recurrently re-computed. Such re-computation effectively provides an adaptive threshold that remains consistent with the user-specified maximum acceptable false alarm rate.

In addition to the fluid accumulation alert described above, the external processor circuit 230 can be capable of computing a representative fluid index value from the daily histogram data array received from the IMD 212. A trend of the representative fluid index value (e.g., over several or many days) can be displayed for the subject, caregiver, or other user. Advantageously, by externally processing the histogram-stored thoracic impedance information, the IMD's 212 battery life may be prolonged. Notably, internal processing of the histogram-stored thoracic impedance information can also be found advantageous in certain situations, such as in situations where closed-loop systems for disease detection and responsive therapy are warranted and desired.

In various examples, the system 200 can include a regimen control circuit 552 configured for initiating or adjusting a regimen to a subject 208 (FIG. 2) at least in part by using thoracic impedance histogram information or an indication of present or impending lung fluid accumulation (e.g., a lung fluid status indication) externally computed from such information and output by a fluid accumulation determination circuit 554. In an example, such regimen includes electrical stimulation, such as cardiac pacing, resynchronization, cardioversion, or defibrillation stimulation, generated by a regimen pulse generator circuit 502 and delivered via one or more electrodes selected by the electrode configuration switch circuit 516. The one or more electrodes can be selected individually or in combination to serve as an anode or a cathode in any unipolar, bipolar or multipolar configuration.

In another example, such regimen is provided elsewhere (e.g., communicated to the nearby external user-interface 216 or delivered via an implantable drug pump 504) and includes, for example, a drug dose, a diet regimen, or a fluid intake regimen. In one example, the drug dose can include a set of one or more drug regimen instructions communicated and displayed on the nearby external user-interface 216, such as in the form of the user-detectable indication 224. In certain examples, the set of drug regimen instructions includes a suggested daily intake schedule of one or more drugs, such as antiotension-converting enzyme (ACE) inhibitors, beta blockers, digitalis, diuretics, vasodilators, or the like. In certain examples, the drug dose can be automatically delivered per the suggested daily intake schedule via the implantable drug pump 504 or another drug dispensing device provided within the IMD 212 or implanted nearby and coupled thereto. In certain examples, the drug dose can be delivered per the suggested daily intake schedule via external (e.g., electronic) drug dispersing devices.

In a similar manner, the diet regimen and the fluid intake regimen can be communicated to the subject 208 via the user-detectable indication 224 of the nearby external user-interface 216. In an example, the diet regimen can include a set of one or more dietary instructions to be followed by the subject 208, such as restriction of sodium to 2 grams or less per day and no more than one alcoholic drink per day. In another example, the fluid intake regimen can include a set of one or more fluid intake instructions to be followed by the subject 208, such as to avoid consuming an excess amount of fluid. FIGS. 5A-5B illustrate just one example of various circuits, devices, and interfaces of the system 200, which are implemented either in hardware or as one or more sequences of steps carried out on a microprocessor or other controller. Such circuits, devices, and interfaces are illustrated separately for conceptual clarity; however, it is to be understood that the various circuits, devices, and interfaces of FIGS. 5A-5B need not be separately embodied, but can be combined or otherwise implemented. As an example, an internal or an external processor circuit can include an input to receive thoracic impedance histogram information, and can be configured to use such information to internally or externally compute and provide a lung fluid status indication.

Figure 6:
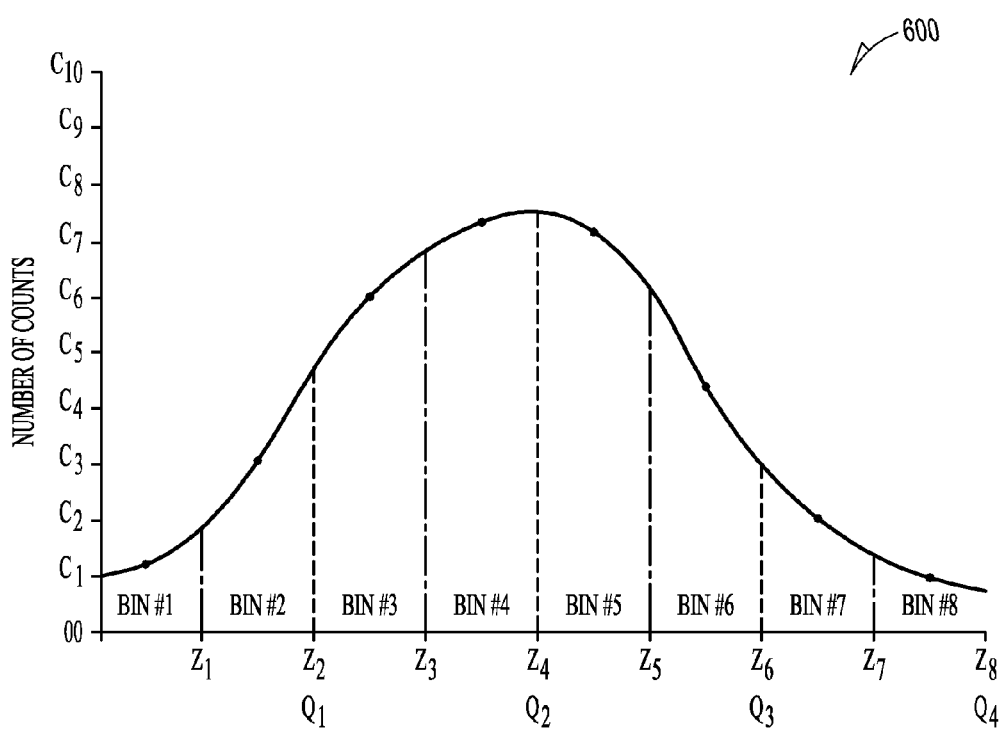
FIG. 6 is a graphical display illustrating an example of a histogram array stored in a memory circuit, information of which can be used by a fluid monitoring system to compute and provide a lung fluid status indication.

FIG. 6 is a graphical display illustrating a histogram 600, such as an intraday histogram, stored in a memory circuit 252 (FIG. 2). The horizontal axis of the histogram 600 lists the impedance bin subranges. The vertical axis indicates the relative number of signal counts present in each subrange. In this example, the histogram 600 includes eight histogram bins (bin #1, bin #2, . . . , bin #8). Each such bin represents a subrange of expected thoracic impedance-indicating signal characteristic amplitude values. Each such bin is configured to quantifiably store the occurrence of numerically inclusive thoracic impedance-indication signals measured by an electrical impedance measurement circuit 250 (FIG. 2). For each thoracic impedance-indication signal value acquired that corresponds to the subrange of a given histogram bin, a count of values for that bin can be incremented. As shown in FIG. 6, bin #1 has a count of approximately $C_1$, bin #2 has a count of approximately $C_3$, bin #3 has a count of approximately $C_5$, bin #4 has a count of approximately $C_7$, bin #5 has a count of approximately $C_7$, bin #6 has a count of approximately $C_4$, bin #7 has a count of approximately $C_2$, and bin #8 has a count of approximately $C_1$. As discussed above, an external processor circuit 230 (FIG. 2) is configured to receive and use such thoracic impedance histogram information to compute and provide a lung fluid status indication.

Figure 7:
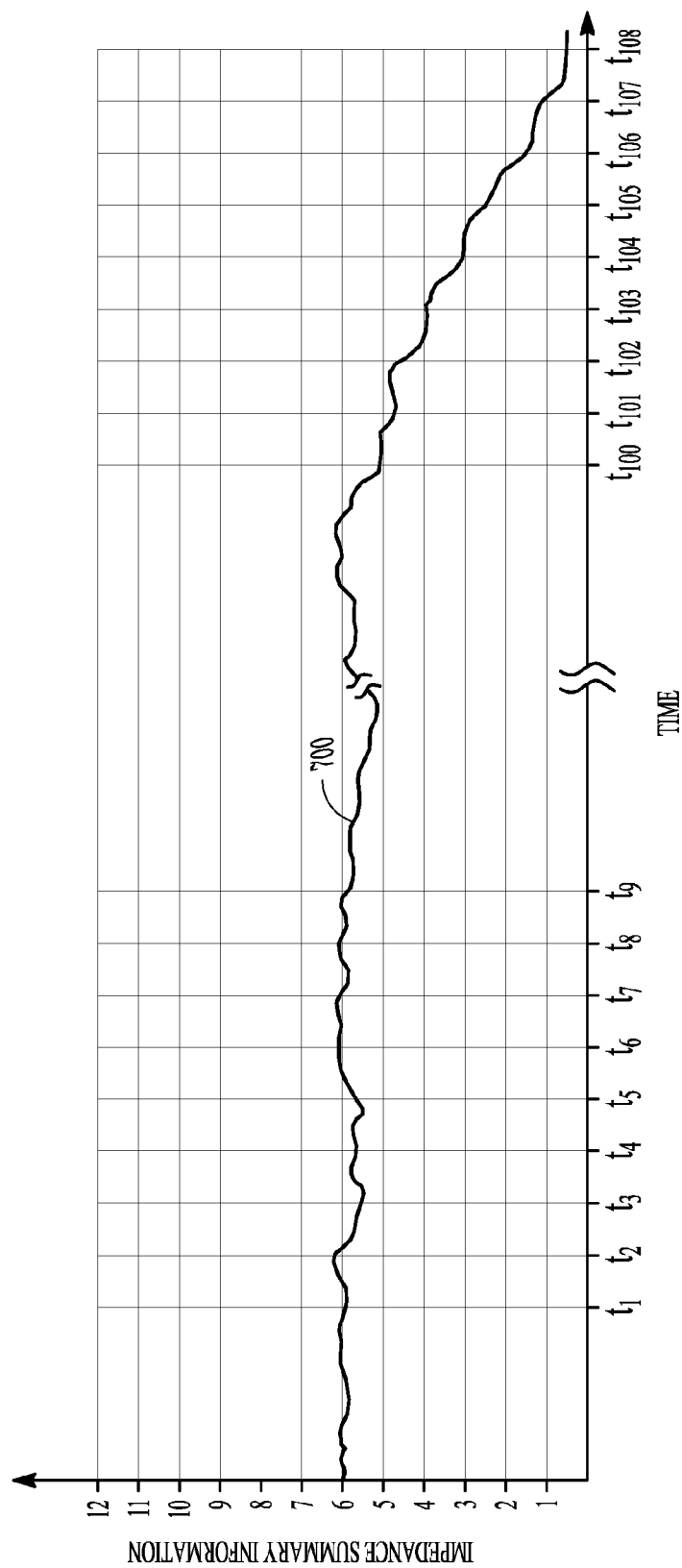
FIG. 7 is a graphical display illustrating an example of a trend over time of information stored in one or more portions of a histogram array, such trend indicative of present or impending fluid accumulation.

FIG. 7 is a graphical display illustrating a conceptualized (not real data) trend 700 over time of impedance summary information computed from one or more portions of a histogram array, such as an upper-quartile portion of the histogram array (see, e.g., bins #7 and #8 of FIG. 6). In the example shown, the impedance summary information from the one or more portions of the histogram array has a decreasing trend over time. A decreasing trend in histogram-based impedance values can indicate present or impending fluid accumulation, such as pulmonary edema. The upper-quartile portion of the histogram array is representative of higher thoracic impedance-indicating signal characteristic values than the remaining quartiles of the histogram array. Thus, a reduction over time in the number of counts, mean, median or the like of the upper quartile portion of the impedance histogram can indicate a shift of the histogram toward lower impedance signal values. This can correlate to an indication of present or impending fluid accumulation in the lungs 204, 206 (FIG. 2). Information about such a decrease can be used by the present system 200 (FIG. 2) to further specify an indication of lung fluid status. The graphical display illustrating the trend 700 over time can be received and displayed on an external user-interface device 216, 218 (FIG. 2), such as on an user-detectable indication screen 224.

Without being bound by theory, the present inventors have recognized that an upper-quartile portion of a histogram may exhibit the largest diurnal variation when comparing thoracic fluid status levels between a healthy (baseline) subject to a fluid overload subject. This is because higher thoracic impedance signal values are typically measured two, three or more hours after a subject wakes from a supine sleep position. After awaking, the subject will often assume some sort of upright posture position in which fluid that has flowed toward the thoracic region during supine sleep slowly drains away from such region over time. For healthy subjects, the increase in thoracic impedance during such time is relatively large; however, for fluid overload subjects, the increase in thoracic impedance may less pronounced. Thus, it is believed that comparing a fluid overload subject's largest measured short-term thoracic impedance-indicating signal characteristic values (e.g., mean or median of the histogram's upper-quartile) or number of upper-quartile bin counts to that of a healthy baseline subject may provide a user with enhanced fluid accumulation status information, such as for determining the presence or absence of pulmonary edema. One or more of a sleep state detector circuit, an activity sensor circuit, or a posture sensor circuit 520 (FIG. 5A) can be used to recognize sleep and awake subject states.

There are a variety of underlying conditions that may lead to thoracic fluid build-up, more specifically pulmonary edema, and a variety of regimen approaches targeting such conditions. The selection of the regimen approach, and the parameters of the particular regimen approach selected, can be a function of the underlying condition and a severity of such condition. For this reason, the present system 200 (FIG. 2) can include a regimen control circuit 550 to appropriately select a regimen given a subject's detected health status.

Figure 8:
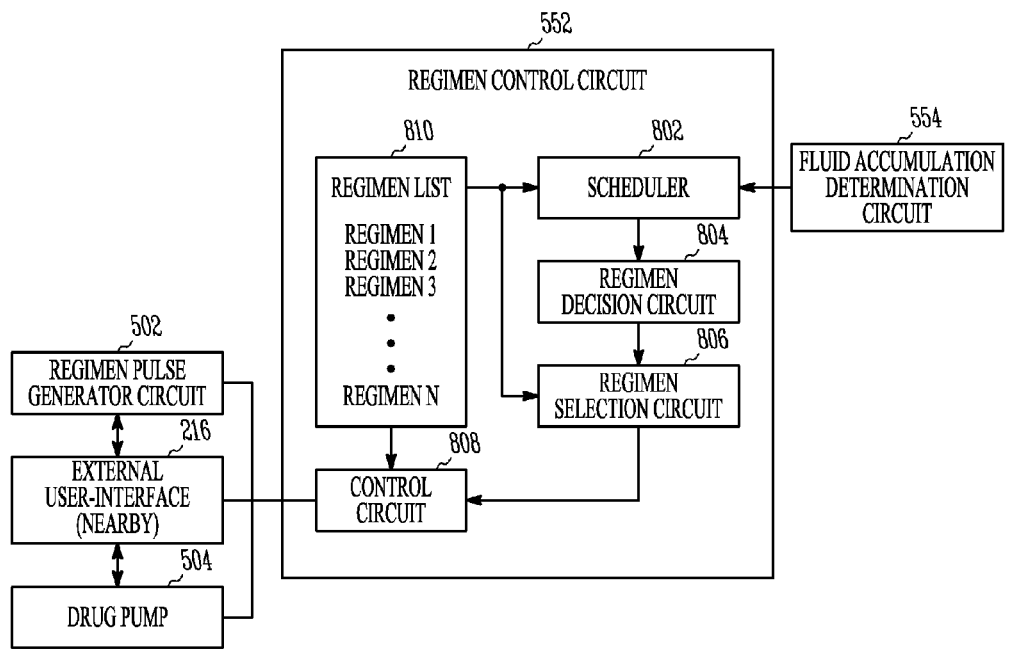
FIG. 8 is a block diagram illustrating an example of a regimen control circuit for use in the present system, the system being configured for monitoring excess fluid accumulation in the thoracic region of a subject using information organized and stored in one or more histogram bins.

FIG. 8 is a block diagram illustrating an example of a regimen control circuit 552, which can be used to trigger one or more regimens (e.g., therapies) to a subject 208 (FIG. 2). A regimen can be triggered in response to thoracic impedance histogram information or a resulting indication of present or impending lung fluid accumulation status indication. The fluid status indication can be externally computed from such information and output by a fluid accumulation determination circuit 554.

The regimen control circuit 552 can include an input that receives the indication of present or impending lung fluid accumulation output from the fluid accumulation determination circuit 552. In an example, a scheduler 802 schedules the indications of present or impending lung fluid accumulation. A regimen decision circuit 804 decides whether some form of regimen is warranted. If a regimen is deemed to be warranted, a regimen selection circuit 806 selects one or more appropriate regimens. A control circuit 808 adjusts the selected regimen via an output to one or more of a regimen pulse generator circuit 502, a nearby external user-interface 216, or a drug pump 504, for example.

The regimen control circuit 552 can include a regimen list 810, which can relate the regimens of such list 810 to the highest contributor(s) to the indication of present or impending lung fluid accumulation. In an example, the regimen list 810 includes all possible disease state preventive regimens or secondarily related regimens that the present system 200 can deliver or communicate to the subject 208. The regimen list 810 can be programmed into an IMD 212 (FIG. 2) either in hardware, firmware, or software and stored in a memory 252 (FIG. 2).

In another example, the regimen list 810 includes immediate, short-term, intermediate-term, or long-term fluid accumulation preventive therapies. Immediate fluid accumulation preventive therapies can include, by way of example, initiating or changing a drug dose administered to the subject via an implantable drug pump 504 or electrical stimulation administered to the subject 208 via the regimen pulse generator circuit 502. Short-term fluid accumulation preventive regimens can include, by way of example, administering a continuous positive air pressure ("CPAP") dose to the subject 208 or notifying a caregiver to initiate or change the subject's drug dose treatment program. Intermediate-term fluid accumulation preventive regimens can include, by way of example, adjusting the subject's 208 lifestyle such as his or her diet or fluid intake regimen. Finally, long-term fluid accumulation preventive regimens can include, by way of example, notifying the subject 208 or caregiver to alter the drug which takes longer to affect the subject (e.g., beta blockers, ACE inhibitors) or administering CRT to the subject 208.

Each member of the regimen list 810 can be associated with a corresponding time of action, which can include information about one or more of a time for the regimen to become effective or a time after which the regimen is no longer effective. In one example, only one member of the regimen list 810 is invoked at any particular time. In another example, one or more combinations of different regimens are provided at substantially the same time. The various subcircuits in the regimen control circuit 552 are illustrated as such for illustrative purposes only; however, these subcircuits can alternatively be incorporated in the fluid accumulation determination circuit 554 or elsewhere, such as being implemented as a set of programmed instructions performed by a general purpose controller or other circuit.

Figure 9:
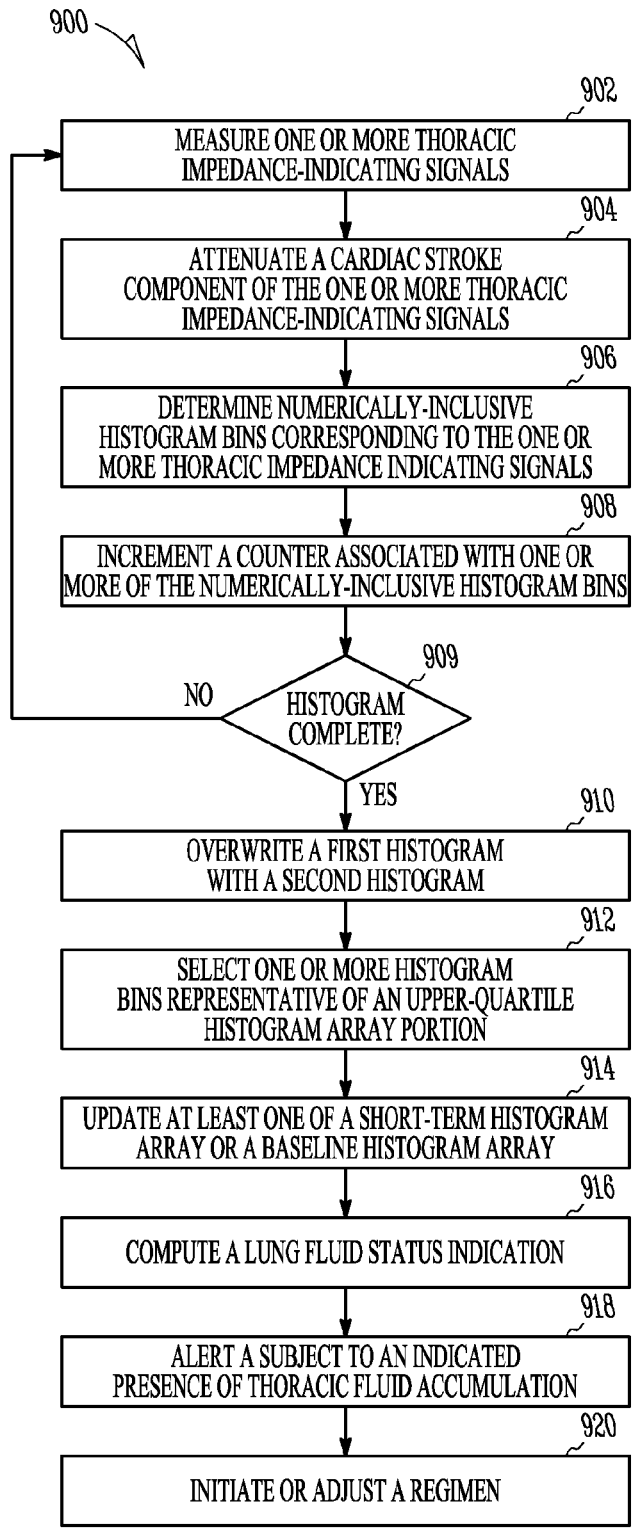
FIG. 9 is a block diagram illustrating an example method of monitoring excess fluid accumulation in the thoracic region of a subject by computing and providing a lung fluid status indication, the indication found using information organized and stored in one or more histogram bins.

FIG. 9 is a block diagram 900 illustrating one example of a method of monitoring excess fluid accumulation in the thoracic region of a subject. This can involve monitoring one or both of a subject's lungs using thoracic impedance histogram information. Each histogram bin represents a subrange of expected thoracic impedance-indicating signal characteristic values. Each histogram bin can be configured to quantifiably store the occurrence of numerically inclusive thoracic impedance-indicating signal characteristic measurements measured by an electrical impedance measurement circuit. At 902, one or more thoracic impedance-indicating signal characteristics including at least a respiration component and a fluid status component are measured. At 904, a cardiac stroke component of the one or more thoracic impedance-indicating signal characteristics is optionally attenuated. In various examples, one or both of a timing circuit or a cardiac sensor circuit is used to synchronize the thoracic impedance-indicating signal characteristic measurements, such as to a refractory portion of a subject's cardiac cycle.

At 906, the one or more thoracic impedance-indicating signal characteristic measurements are compared to histogram bin subranges to identify an appropriate histogram bin for the measurement. At 908, a bin count of the appropriate histogram bin is optionally incremented, such as by incrementing a histogram bin counter or memory location stored count value. At 909, a decision is made as to whether or not complete histogram information has been obtained. If not, the process returns to 902. If it is determined that complete histogram information has been obtained, the process continues to 910. At 910, a first histogram is optionally overwritten with a later second histogram. In this way, newly acquired histograms can overwrite older histograms, such as to prolong battery life of a device associated with the memory storage device.

At 912, one or more histogram bins representative of an upper-quartile histogram portion or an intra-quartile range are optionally selected and processed, such as via a processor circuit (see at 916). At 914, one or both of a short-term histogram or a baseline histogram is optionally updated using information about thoracic impedance-indicating signal characteristic measured over a period of time. The short-term and baseline histograms can be used to compute and provide a lung fluid status indication. In various examples, the lung fluid status indication provides an indication of the presence or absence of a thoracic fluid accumulation event, such as a pulmonary edema event.

At 916, the lung fluid status indication is internally or externally computed using thoracic impedance histogram information. In one example, histogram bin count information from a particular intraday histogram is used to compute the lung fluid status indication. In another example, a plurality of intraday histograms are aggregated and used to compute the lung fluid status indication. In yet another example, the lung fluid status indication is computed using a deviation between one or more histogram bins of a short-term histogram array and one or more corresponding histogram bins of a baseline histogram array.

At 918, a subject is alerted to a detected presence of thoracic fluid accumulation if the computed lung fluid status indication is beyond some programmed limit. At 920, a regimen for application to the subject is initiated or adjusted in response to the computed lung fluid status indication.

CONCLUSION

Chronic diseases, such as heart failure, require close medical management to reduce hospitalizations, morbidity and mortality, as subjects with heart failure live in a delicate balance. Because such disease status evolves with time, frequent caregiver follow-up examinations are often necessary. This conventional approach of periodic follow-up is unsatisfactory for diseases like heart failure, in which acute, life-threatening exacerbations, such as pulmonary edema, can develop between follow-up examinations. Pulmonary edema is a serious medical condition in which an excess amount of fluid accumulates in or around a subject's lungs. This condition can, and often does, result from heart failure. Pulmonary edema can require immediate care. While it can sometimes prove fatal, the outlook for subjects possessing pulmonary edema can be good upon early detection and prompt treatment.

Advantageously, the present systems and methods may provide for enhanced thoracic fluid monitoring via less complex data processing and thus, may provide a timelier, more accurate, and potentially cheaper detection of pulmonary edema or other thoracic fluid accumulation than is currently available. In this way, caregivers and heart failure subjects can be provided with a better tool to manage pulmonary edema, and ultimately, heart failure. Such detection is made possible by, among other things, storing at least one thoracic impedance-indicating signal characteristic in one of a number of histogram bins, each histogram bin numerically representing a different subrange of thoracic impedance-indicating signal characteristic values from a range of expected signal values. In one example, thoracic fluid monitoring is made less complex by using information about a count of thoracic impedance signal values stored in one or more of the histogram bins to compute a lung fluid status indication. In another example, thoracic fluid monitoring is made more accurate by using information about a selected portion of a histogram array, such as information about an upper-quartile portion or intra-quartile portion of the histogram array, to compute the lung fluid status indication.

Closing Notes

The above Detailed Description includes references to the accompanying drawings, which form a part of the Detailed Description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "implantable medical device" or simply "IMD" is used to include, but is not limited to, implantable cardiac rhythm management (CRM) systems such as pacemakers, cardioverters/defibrillators, pacemakers/defibrillators, biventricular or other multi-site resynchronization or coordination devices such as cardiac resynchronization therapy (CRT) device, subject monitoring systems, neural modulation systems, and drug delivery systems. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine-implemented or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more features thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. In addition, while the majority of this patent document discusses the monitoring of fluid in a thoracic region of a subject, the present systems and methods can be used in ways similar to those discussed herein to monitor fluid accumulation in other regions of a subject's body. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A system comprising:
   an implantable medical device including,
      an electrical impedance measurement circuit configured to measure one or more thoracic impedance-indicating signal characteristics, including at least a liquid status component, using information about electrical energy injected between two or more electrodes and a potential difference created thereby between the same or different two or more electrodes; and
      a memory circuit including a number of histogram bins, each bin representing a subrange of thoracic impedance-indicating signal characteristic values, including values indicative of a liquid status, the memory circuit configured for storing a count representative of the one or more thoracic impedance-indicating signal characteristics, including at least the liquid status component, into a histogram bin having a numerically inclusive subrange; and
   a processor circuit including an input to receive and use information about the count representative of the one or more thoracic impedance-indicating signal characteristics, including at least the liquid status component, stored in the histogram to provide a lung edema status indication.

2. The system of claim 1, comprising a trigger circuit to trigger a thoracic impedance-indicating measurement synchronized with a refractory portion of a subject's cardiac cycle, wherein the trigger circuit comprises at least one of a timing circuit or a cardiac sensor circuit.

3. The system of claim 1, comprising a posture sensor configured to produce a posture signal indicative of a posture of a subject, the posture sensor configured to trigger a thoracic impedance-indicating measurement when the posture signal is indicative of a upright orientation.

4. The system of claim 1, wherein the memory circuit includes a counter circuit configured to increment the count of a histogram bin.

5. The system of claim 4, wherein the processor circuit is configured to use information about the count of the histogram bin to compute and provide the lung edema status indication.

6. The system of claim 1, comprising a histogram-selective circuit configured to select one or more histogram bins representative of a reduced subrange of the histogram.

7. The system of claim 6, wherein the processor circuit is configured to use information about a count or a value representative of the reduced subrange to compute and provide the lung edema status indication, wherein the reduced subrange represents an upper-percentile of the histogram or an intra-percentile range of the histogram.

8. The system of claim 7, wherein the information about the count or the value representative of the reduced subrange includes information about a central tendency of one or more values stored in the selected one or more histogram bins, which are representative of the reduced subrange.

9. The system of claim 1, comprising a comparator circuit configured to compute a deviation between one or more histogram bins previously received from the memory circuit and one or more corresponding baseline histogram bins having the same numerical subrange; and
   wherein the processor circuit is configured to use information about the deviation to compute and provide the lung edema status indication.

10. The system of claim 9, wherein the deviation is indicative of a difference in the number of counts from the corresponding baseline histogram bin.

11. The system of claim 9, wherein the deviation is between an average of thoracic impedance signal characteristic data of the one or more histogram bins previously received and thoracic impedance signal characteristic data of the one or more baseline histogram bins.

12. The system of claim 1, comprising an external user-interface device communicatively coupled to the implantable medical device and including a user-detectable indication,
   the user-detectable indication configured to provide a display of at least one of received information about thoracic impedance signal characteristic data of one or more histogram bins, a deviation trend between such received information and corresponding information of one or more baseline histogram bins, or the computed lung edema status indication.

13. The system of claim 1, wherein the one or more thoracic impedance-indicating signal characteristics include a respiration status component.

14. A method comprising:
  measuring a thoracic impedance-indicating signal characteristic including a liquid status component;
  storing a count representative of the thoracic impedance-indicating signal characteristic, including the liquid status component, in a histogram that includes a plurality of histogram bins representing corresponding subranges of thoracic impedance-indicating signal characteristic values, including values indicative of a liquid status; and
  computing and providing a lung edema status indication using histogram information about the count representative of the thoracic impedance-indicating signal characteristic, including the liquid status component.

15. The method of claim 14, comprising attenuating a cardiac stroke component of the thoracic impedance-indicating signal, including synchronizing the thoracic impedance-indicating signal measurement to a specified portion of a subject's cardiac cycle.

16. The method of claim 14, comprising selecting one or more histogram bins representative of a subrange of the histogram; and
  using information about a count or a value representative of the one or more bins representative of the subrange to provide the lung edema status indication.

17. The method of claim 14, comprising overwriting a first histogram comprising first histogram bins with a second histogram comprising second histogram bins, the second histogram comprising data acquired later in time than for the first histogram array.

18. The method of claim 14, comprising initiating or adjusting a regimen in response to the lung edema status indication.

19. The method of claim 14, comprising triggering the thoracic impedance-indicating signal characteristic measurement when a posture signal indicative of a upright orientation is measured.

20. The method of claim 14, wherein storing the count-representative of the thoracic impedance-indicating signal characteristic includes incrementing a count associated with a histogram bin; and
  wherein computing the lung edema status indication includes using count information from the histogram.

21. The method of claim 20, comprising aggregating count information from each of the histogram bins; and
  using the aggregated count information to compute the lung edema status indication.

22. The method of claim 14, wherein storing the count representative of the thoracic impedance-indicating signal characteristic includes storing the count representative of the thoracic impedance-indicating signal characteristic into a bin of an intraday histogram.

23. The method of claim 22, comprising aggregating thoracic impedance-indicating signal characteristic information from a plurality of intraday histograms; and
  using the aggregated thoracic impedance signal characteristic information to compute the lung edema status indication.

24. The method of claim 14, wherein computing the lung edema status indication includes computing a deviation between at least one histogram bin of a short-term histogram and at least one corresponding histogram bin of a baseline histogram.

25. The method of claim 24, comprising updating the short-term histogram using a count representative of a first thoracic impedance-indicating signal characteristic measured over a first time period; and
  updating the baseline histogram using a count representative of a second thoracic impedance-indicating signal characteristic, which is the same or different than the first thoracic impedance-indicating signal, measured over a second time period that is longer than the first time period.

26. The method of claim 14, wherein computing the lung edema status indication includes recognizing whether a thoracic liquid accumulation event is present.

* * * * *